United States Patent [19]

O'Neill

[11] 4,205,683
[45] Jun. 3, 1980

[54] ADAPTER FOR INFLATING BALLOON CATHETER

[75] Inventor: William J. O'Neill, Milltown, N.J.

[73] Assignee: Victory Engineering Corporation, Springfield, N.J.

[21] Appl. No.: 887,818

[22] Filed: Mar. 17, 1978

Related U.S. Application Data

[63] Continuation-in-part of Ser. No. 757,660, Jan. 1, 1977, Pat. No. 4,088,135.

[51] Int. Cl.² ............................................. A61M 25/00
[52] U.S. Cl. ............................... 128/348; 128/349 BV
[58] Field of Search ............................... 128/348–351, 128/246, 325, 344

[56] References Cited

U.S. PATENT DOCUMENTS

| | | | |
|---|---|---|---|
| 3,211,150 | 10/1965 | Foderick | 128/349 BV |
| 3,211,151 | 10/1965 | Foderick et al. | 128/349 B |
| 4,088,135 | 5/1978 | O'Neill | 128/348 |

*Primary Examiner*—Dalton L. Truluck
*Attorney, Agent, or Firm*—Walter R. Keller

[57] ABSTRACT

An adapter for use with a coaxial activating syringe balloon catheter assembly is provided with a simplified slide valve which permits a precise amount of fluid to be introduced into the balloon and held therein. The fluid is injected by means of a metering syringe which can thereafter be removed without deflating the balloon. A simple longitudinal movement of the adapter will release the fluid pressure in the balloon for deflation when desired.

6 Claims, 3 Drawing Figures

U.S. Patent  Jun. 3, 1980  4,205,683
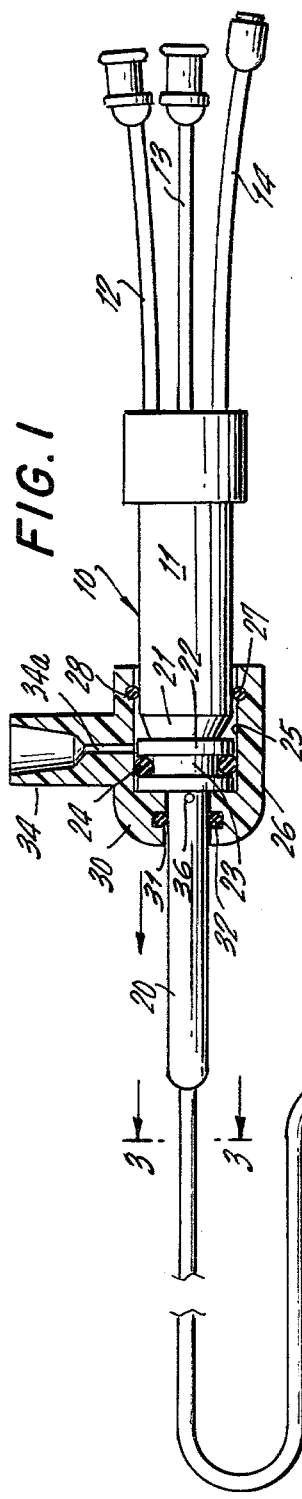
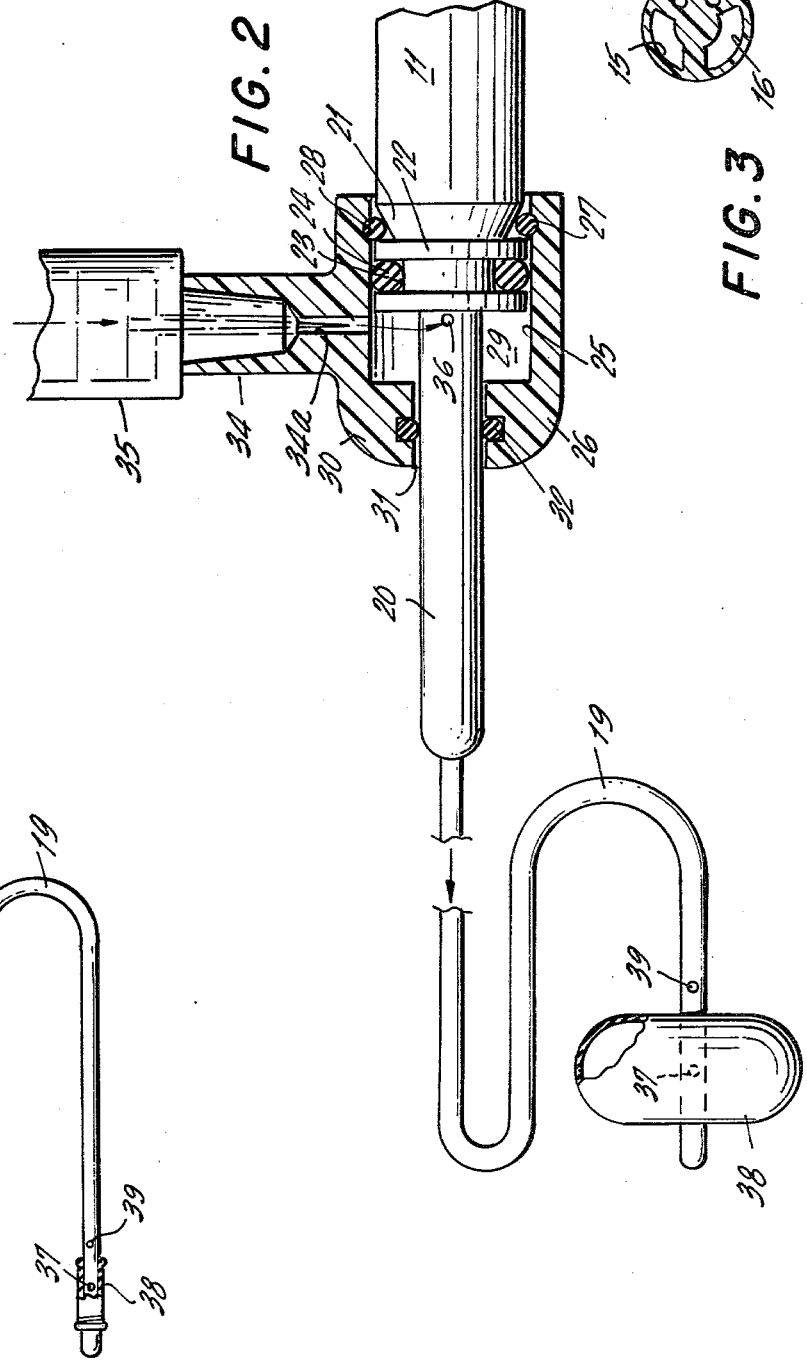

ADAPTER FOR INFLATING BALLOON CATHETER

BACKGROUND OF THE INVENTION

This application is a continuation in part of an application entitled Balloon Catheter With Coaxial Activating Syringe Ser. No. 757,660 filed Jan. 1, 1977 U.S. Pat. No. 4,088,135 issued May 9, 1978 to by William J. O'Neill.

In the use of Foley or Balloon catheters, it is often desired to use a fluid or $CO_2$ rather than air for inflating the balloon. Such inflating devices must supply a specific amount of fluid to the balloon to prevent over stressing the balloon and causing balloon failure. Before the catheter is removed, the balloon must be deflated. These steps must be carried out with ease and preferably by the employment of a minimum amount of structure.

Balloon inflating apparatus for catheters has been disclosed by Swanson, U.S. Pat. No. 3,409,015; Stark et. al., U.S. Pat. No. 3,448,739; Bleeker, U.S. Pat. No. 3,818,903; Nozick, U.S. Pat. No. 3,923,065, and Hasson, U.S. Pat. No. 3,948,270. Such devices, however, have been cumbersome, often complicated in their construction, and rely heavily upon the skill of the user to insure their proper function.

Accordingly, it is an object of the present invention to provide an adapter for incorporation into a balloon catheter apparatus which will permit a precise amount of a fluid to be directed into the balloon.

A further object of the present invention is to provide a balloon inflating adapter in which the syringe containing the inflating fluid can be removed easily after use, without loss of the balloon inflating fluid.

Still another object of the present invention is to provide a simple, finger operated structure to deflate the balloon.

A feature of the present invention is its unitary "T" shaped structure which reduces its size and weight requirements.

Another feature of the present invention is its slide valve construction for control of the inflating fluid.

A further feature of the present invention is its use of a Leur lock fitting for ready engagement and disengagement of the fluid applying syringe.

SUMMARY

In the embodiment described and shown herein, a hollow adapter is slidably carried upon the distal portion of the elongated body of a balloon catheter assembly. A small piston is formed upon the distal end of the body, which piston serves to regulate the passage of fluid through the adapter and into or out of the balloon at the distal end of an elongated lumen. A hollow lateral portion on the adapter is provided with a Luer lock fitting in communication with the interior of the adapter to permit fluid to be introduced or removed from the balloon.

BRIEF DESCRIPTION OF THE DRAWING

In the accompanying drawing, forming part hereof, similar parts have been given the same reference numbers, in which drawing:

FIG. 1 is a view in side elevation, partly in section and partly broken away of one complete embodiment of the present invention.

FIG. 2 is a fragmentary view, somewhat enlarged, of the adapter structure shown in FIG. 1 with the apparatus in the fluid applying mode.

FIG. 3 is a cross-sectional view of the lumen taken on line 3—3 in FIG. 1.

DESCRIPTION OF THE INVENTION

Referring to the drawing, there is shown a balloon catheter assembly 10 having an elongated cylindrical body portion 11. Fluid bearing tubes 12, 13 and electrical leads 14 are led through the catheter body portion 11 and communicate with openings 15, 16, 17 in an elongated lumen 19. The manner and purpose of the tubes 12, 13 and electrical leads 14 vary greatly, are well known in the catheter art, and need not be further discussed.

An elongated hollow cylindrical guide 20 of reduced diameter is provided on the distal end of the body portion 11 and may be integral with the body portion. The distal end of the body portion 11 is further beveled as indicated at 21 and a small piston 22 is formed or secured between the distal end of the bevel 21 and the guide 20. The piston is grooved at 23 to receive an elastomeric "O" ring 24. While the piston is of a diameter which will permit it to slide freely within the hollow body 25 of the adapter 26, the "O" ring forms a fluid tight seal between the piston and the said bore.

A retaining ring 27 preferable made of an elastomer is carried by an annular recess 28 in the adapter body 25 near the proximal end thereof. The retaining ring limits the adapter in its movement along the catheter body portion 11 by engaging flange 22 when the catheter is in the fluid applying position.

At the distal end of the adapter 26 there is a thickened end wall 30 having an axial bore 31 to freely receive the elongated cylindrical guide 20. A second "O" ring 32 is positioned within an annular recess 33 in the end wall 30 and in sealing contact with the elongated cylindrical guide 20.

As best shown in FIGS. 1 and 2, the adapter body 25 is somewhat "T" shaped by reason of a laterally disposed Luer lock fitting 34 integral with the adaptor body. The fitting 34 is in communication with the chamber 29 within the adapter body 25 through an entrance port 34a. The piston 22 forms a slide valve within the chamber 29 beneath the Luer fitting 34. Fluid introduced into the fitting 34 by a syringe 35, as shown in FIG. 2, can thus enter the chamber 29 through the port 34a from which it can pass through the lateral opening 36 in the guide 20, through the opening 18 in the lumen 19, and out of a second lateral opening 37 in the lumen to inflate the balloon 38 which overlies the second opening 37. The precise amount and type of fluid necessary to inflate but not overstress the balloon 38 can be precisely applied by the syringe 35 when the adapter is in the position shown in FIG. 2. Thereafter, the adapter 26 can be slid along the body portion 11 and guide 20 until it reaches the position shown in FIG. 1. At this juncture, the fluid in the balloon is sealed off and the balloon will remain inflated. Medication or other fluids can be applied through the the lumen using the fluid bearing tubes 12, 13 and lateral openings 39 in the well-known manner.

Once the balloon 38 is inflated and the adapter shifted to the sealing position of FIG. 1, the syringe 35 can be removed from the assembly, thus reducing the bulk of the apparatus and improving the handling characteristics of the catheter.

When it is desired to remove the catheter, the adapter is slid from the position of FIG. 1 to that of FIG. 2. This operation can be achieved without releasing hold of the catheter body portion 11. The balloon inflating fluid will then pass through the second opening 37, the lumen opening 18, the first opening 36, the chamber 29 and out through the Luer fitting 34.

From the foregoing it will be seen that there has been provided an adapter for use with a balloon catheter of simplified structure and operation which permits of precise metering of the amount of fluid applied to inflate the balloon. Any desired fluid may be used for inflation. Moreover, deflation of the balloon is accomplished by a simple sliding action.

Having thus fully described the invention, what is claimed and desired to be secured by Letters Patent is:

1. An adapter for a balloon catheter having a coaxial body portion, an elongated hollow cylindrical guide extending from the distal end of the body portion, an elongated lumen in communication with the interior of the said guide and an inflatable balloon carried around and near the distal end of the lumen, the interior of said balloon being in communication with the interior of the lumen said adapter comprising a hollow substantially "T" shaped body, a centrally bored end wall on the distal end of said body receiving the cylindrical guide therethrough, an annularly grooved piston between the coaxial body portion and the said cylindrical guide slidably received within the hollow "T" shaped body, a first sealing means between the piston and interior of the "T" shaped body, a retaining ring between the coaxial body portion and the interior of the "T" shaped body, a second sealing means between the cylindrical guide and the interior of the "T" shaped body, an opening means in the cylindrical guide between the first and second sealing means in fluid communication with the interior of said guide, and a tapered two diameter bored lock fitting in the "T" shaped body in communication with the interior of said body whereby fluid may be introduced into the catheter to inflate and deflate the balloon.

2. An adapter according to claim 1 in which the first sealing means is carried within the piston groove.

3. An adapter according to claim 1 in which the piston is reciprocable beneath an entrance port at the bottom of the Luer fitting.

4. An adapter according to claim 2 in which the first sealing means is an "O" ring.

5. An adapter according to claim 1 in which the retaining ring is an elastomer and the "T" shaped body is recessed to receive the said second sealing means.

6. An adapter according to claim 1 in which the second sealing means is carried by the end wall and the end wall is recessed to receive the said second sealing means.

* * * * *